(12) United States Patent
Shimizu

(10) Patent No.: US 6,836,533 B2
(45) Date of Patent: Dec. 28, 2004

(54) MULTI-LAYER FILM SPECTROSCOPIC ELEMENT FOR BORON FLUORESCENE X-RAY ANALYSIS

(75) Inventor: Kazuaki Shimizu, Takatsuki (JP)

(73) Assignee: Rigaku Industrial Corporation, Osaka (JP)

( * ) Notice: Subject to any disclaimer, the term of this patent is extended or adjusted under 35 U.S.C. 154(b) by 156 days.

(21) Appl. No.: 10/258,845
(22) PCT Filed: May 30, 2002
(86) PCT No.: PCT/JP02/05317
§ 371 (c)(1), (2), (4) Date: Oct. 29, 2002
(87) PCT Pub. No.: WO02/101368
PCT Pub. Date: Dec. 19, 2002

(65) Prior Publication Data
US 2004/0022354 A1 Feb. 5, 2004

(30) Foreign Application Priority Data
Jun. 11, 2001 (JP) .................................. 2001-175642
Aug. 2, 2002 (JP) .................................. 2002-032537

(51) Int. Cl.⁷ ............................................. G21K 1/06
(52) U.S. Cl. ............................. 378/84; 378/42; 378/44
(58) Field of Search ......................... 378/84, 85, 82, 378/42, 44, 70

(56) References Cited

U.S. PATENT DOCUMENTS 4,785,470 A * 11/1988 Wood et al. .................. 378/84
5,163,078 A * 11/1992 Iketaki .......................... 378/85
5,265,143 A * 11/1993 Early et al. .................... 378/84
5,485,499 A * 1/1996 Pew et al. ..................... 378/84
6,160,867 A * 12/2000 Murakami .................... 378/84
6,396,900 B1 * 5/2002 Barbee et al. ................ 378/84

FOREIGN PATENT DOCUMENTS

| JP | 62-226047 A | 10/1987 |
| JP | 11-258396 A | 9/1999 |
| JP | 11-295245 A | 10/1999 |
| JP | 2000-147197 A | 5/2000 |
| JP | 2000-147999 A | 5/2000 |
| JP | 2000-241593 A | 9/2000 |
| WO | WO 00/75646 A2 | 12/2000 |

* cited by examiner

Primary Examiner—Craig E. Church
Assistant Examiner—Irakli Kiknadze
(74) Attorney, Agent, or Firm—Birch, Stewart, Kolasch & Birch, LLP

(57) ABSTRACT

There is provided a multilayered spectroscopic device effective to achieve in a short length of time the highly accurate fluorescent X-ray analysis of boron wherein the influence that may be brought about by the interfering X-rays and the background is sufficiently reduced and the strength of reflection of B-Kα line is sufficient. In this multilayered spectroscopic device 3, lanthanum (La), an alloy containing lanthanum as a principal component or lanthanum oxide ($La_2O_3$) is used for the reflecting layers 31 and boron is used for the spacer layers 32 and the periodic length d is chosen to be within the range of 7 to 14 nm and the film thickness ratio of the reflecting layers 31 to the spacer layers 32 is chosen to be within the range of 2/3 to 3/2. It has a total laminated film thickness t of a value sufficient to allow the strength of reflection of B-Kα line to be equal to or higher than 98% of a saturation value.

3 Claims, 4 Drawing Sheets

MULTI-LAYER FILM SPECTROSCOPIC ELEMENT FOR BORON FLUORESCENE X-RAY ANALYSIS

This application is the national phase under 35 U.S.C. § 371 of PCT International Application No. PCT/JP02/05317 which has an International filing date of May 30, 2002, which designated the United States of America.

APPLICABLE FIELD OF TECHNOLOGY

The present invention relates to a multilayered spectroscopic device for use in fluorescent X-ray analysis of boron, of a kind wherein a plurality of layer pairs each pair including a reflecting layer and a spacer layer are laminated on a substrate.

BACKGROUND ART

As a spectroscopic device for B-Kα line (Wavelength: 6.76 nm) during fluorescent X-ray analysis of boron, the multilayered spectroscopic device has hitherto been known in which reflecting layers are made of molybdenum (Mo) and spacer layers are made of boron carbide ($B_4C$). However, to achieve a highly accurate fluorescent X-ray analysis of boron in a short length of time, with the Mo/$B_4C$ based multilayered spectroscopic device B-Kα line do not give rise to a sufficient strength of reflection and neither interfering X-rays such as the third-order reflection of O-K line nor background such as Si-L line can be suppressed sufficiently. In contrast thereto, the published International Application WO 00/75646 A2 addresses that if lanthanum (La) and boron carbide are used for each of the reflecting layers of the multilayered spectroscopic device and for each of the spacer layers of the same multilayered spectroscopic device, respectively, the strength of reflection of B-Kα line can be increased as compared with that exhibited by the Mo/$B_4C$ based spectroscopic device. Also, it is known that the theoretical calculation has revealed that the use of lanthanum and boron for the reflecting and spacer layers of the multilayered spectroscopic device is effective to increase the strength of reflection of B-Kα line can be increased as compared with that exhibited by the Mo/$B_4C$ based spectroscopic device.

DISCLOSURE OF THE INVENTION

However, even with the La/$B_4C$ based multilayered spectroscopic device, the strength of reflection of B-Kα line is still insufficient in order to achieve in a short length of time the highly accurate fluorescent X-ray analysis of boron. Also, with respect to the La/B based multilayered spectroscopic device, it is only known from the theoretical calculation that as compared with the Mo/$B_4C$ based multilayered spectroscopic device the strength of reflection of B-Kα line can be increased, and it has been difficult to manufacture the multilayered spectroscopic device by finding specific conditions under which the strength of reflection of B-Kα line can be sufficiently increased and, at the same time, reducing any possible influence brought about by the interfering X-rays and the background.

The present invention has been devised with a view to the foregoing problems and is intended to provide a multilayered spectroscopic device effective to achieve in a short length of time the highly accurate fluorescent X-ray analysis of boron wherein the influence that may be brought about by the interfering X-rays and the background is sufficiently reduced and the strength of reflection of B-Kα line is sufficient.

In order to accomplish the above described object, the present invention provides a multilayered spectroscopic device utilizable in fluorescent X-ray analysis of boron contained in a sample and including a substrate on which a plurality of layer pairs each pair including a reflecting layer and a spacer layer are laminated, wherein lanthanum (La), an alloy containing lanthanum as a principal component or lanthanum oxide ($La_2O_3$) is used for each of the reflecting layers and boron is used for each of the spacer layers, a periodic length is within the range of 7 to 14 nm and a film thickness ratio of the reflecting layers to the spacer layers is within the range of 2/3 to 3/2, and wherein the multilayered spectroscopic device has a total laminated film thickness sufficient to allow a strength of reflection of B-Kα line to attain a value equal to or higher than 98% of a saturation value.

With this structure, as compared with the conventional Mo/$B_4C$ based multilayered spectroscopic device it is possible to increase the strength of reflection of B-Kα line by a factor of about 2.2 to 3.8 while the influence brought about by the interfering X-rays such as third-order reflection of O-K line and the background such as Si-L line can be sufficiently reduced and, on the other hand, as compared with the conventional La/$B_4C$ based multilayered spectroscopic device it is possible to increase the strength of reflection of B-Kα line by a factor of about 1.3 and, accordingly, it is possible to accomplish the fluorescent X-ray analysis of boron highly accurately in a short length of time. Preferably, the total laminated film thickness is within the range of 280 to 320 nm and the film thickness ratio of the reflecting layers relative to the spacer layers is preferably about equal to 1 and within the range of 4/5 to 5/4.

BEST MODE FOR CARRYING OUT THE INVENTION

Figure 1:
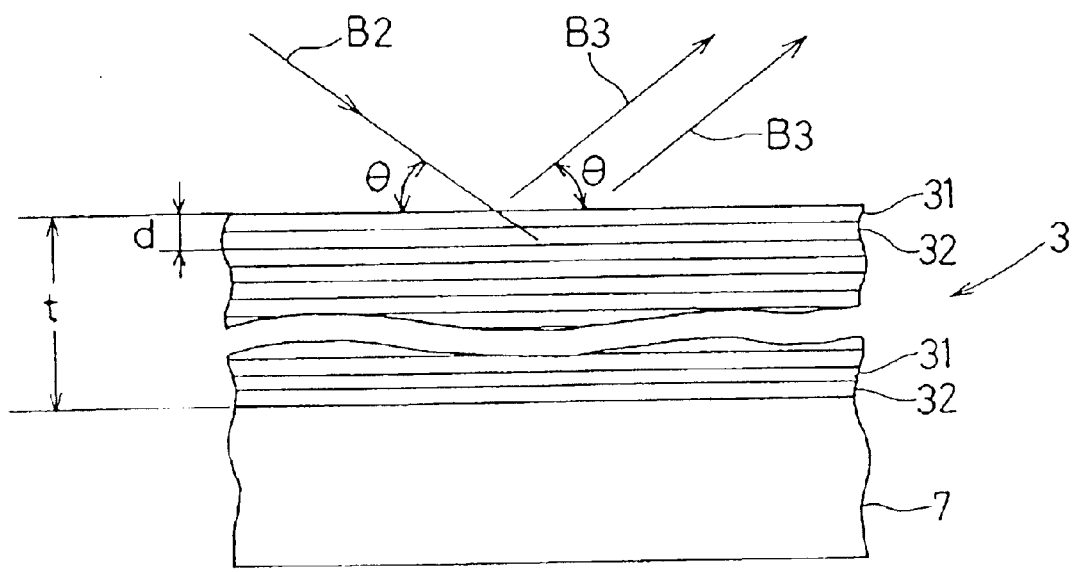
FIG. 1 is a diagram showing a multilayered spectroscopic device for fluorescent X-ray analysis of boron according to a preferred embodiment of the present invention.

Hereinafter, description will be made in connection with a multilayered spectroscopic device for fluorescent X-ray analysis of boron according to a preferred embodiment of the present invention. As shown in FIG. 1, this spectroscopic device is a multilayered spectroscopic device 3 for use in fluorescent X-ray analysis of boron (B) contained in a sample, which device includes a substrate 7 in the form of a silicon wafer on which a plurality of layer pairs each pair including a reflecting layer 31 made of lanthanum (La) and a spacer layer 32 made of boron (B) are formed in a stacked fashion by means of an ion beam sputtering film forming technique. Namely, secondary X-rays B2 such as fluorescent X-rays emitted from the sample are incident at a predetermined angle of incidence (angle of diffraction) θ and B-Kα line B3 representative of the fluorescent X-rays emitted from boron are reflected (diffracted or dispersed) at an angle equal to the angle of incidence θ.

Selection of such specific materials for the reflecting layers 31 and the spacer layers 32 is based on such an assumption that according to the theoretical calculation, the strength of reflection of B-Kα line can be increased to a value greater than that exhibited by any of the conventional Mo/B$_4$C based and La/B$_4$C based multilayered spectroscopic devices. However, by the same reasoning, the material that can be employed for the reflecting layers 31 may include an alloy containing lanthanum as a principal component mixed with molybdenum (Mo) or ruthenium (Ru), or a lanthanum oxide (La$_2$O$_3$). Some examples of use of those different materials for the reflecting layers 31 will be discussed later.

The reason for the use of the ion beam sputtering film forming technique is as follows. Specifically, as discussed previously, although according to the theoretical calculation, it has been known that the use of lanthanum and boron for the reflecting and spacer layers of the multilayered spectroscopic device, respectively is effective to increase the strength of reflection of B-Kα line as compared with that exhibited by the Mo/B$_4$C based spectroscopic device, boron is a semiconductor that can be substantially regarded as a dielectric material and, therefore, unlike boron carbide (B$_4$C) that has been used as a material for the conventional spacer layers and that is considered a good electroconductive material, film forming by the use of any standard deposition technique has been considered difficult to achieve and it has been considered extremely difficult to secure an extremely thin film having a sufficiently small roughness. In view of this, when the ion beam sputtering film forming technique effective to form a film relatively easily even with a dielectric material is employed, it has been found that a flat, extremely thin film of boron can easily be formed and, accordingly, such ion beam sputtering film forming technique is employed in the manufacture of the multilayered spectroscopic device according to the embodiment now under discussion. However, the present invention is not always limited to the use of the ion beam sputtering film forming technique, but any other suitable film forming technique such as a high frequency magnetron sputtering technique or a laser beam deposition technique can be equally employed.

In the embodiment now under discussion, the film thickness ratio of the reflecting layer 31 relative to the spacer layer 32 is chosen to be 1 by the following reason. In the first place, as shown in Table 1 below, five La/B based multi-layered spectroscopic devices were prepared and for each of those spectroscopic devices the strength of reflection of B-Kα line was measured, followed by calculation of the reflection strength ratio (the relative reflection strength) with the conventional Mo/B$_4$C based multilayered spectroscopic device. On the other hand, for comparison purpose, one conventional La/B$_4$C based multilayered spectroscopic device was prepared and the strength of reflection of B-Kα line was similarly measured, followed by calculation of the reflection strength ratio (the relative reflection strength) with the conventional Mo/B$_4$C based multilayered spectroscopic device.

| Materials for Multilayered Spectroscopic Devices | Cycle Length (nm) | Film Thickness Ratio (La:B) | Number of Layer Pairs (pairs) | Relative Reflection Strength (as compared with the Convention) |
|---|---|---|---|---|
| La/B | 8 | 1:2 | 45 | 1.82 |
|  | 8 | 1:1 | 40 | 2.21 |
|  | 8 | 1:1 | 30 | 2.13 |
|  | 8 | 1:1 | 15 | 1.66 |
|  | 13 | 1:1 | 24 | 3.77 |
| La/B$_4$C | 8 | 1:1 | 40 | 1.74 |

According to this, it is clear that the relative reflection strength is large when the periodic length, representative of the thickness of a single layer pair, is chosen to be 8 nm, the number of the layer pairs is chosen to be not smaller than 30, as is the case with the conventional Mo/B$_4$C based multilayered spectroscopic device (Compare the top three rows in Table 1), and the film thickness ratio of the reflecting layers 31 relative to the spacer layers 32 is chosen to be 1:1, rather than 1:2 that is used in the conventional multilayered spectroscopic device. The reason that the relative reflection strength decreases when the film thickness ratio is 1:2 appears to have resulted from the fact that the lanthanum reflecting layers that have been thinned were transformed into a compound with the spacer layers due to a high reactivity, accompanied by deterioration of the optical contrast between them. On the other hand, if the thickness of the reflecting layers is increased, the absorbability tends to increase, accompanied by reduction in relative reflection strength and, therefore, increase of the thickness of the reflecting layers is not feasible. In view of the foregoing, in the illustrated embodiment, with a view to increasing the strength of reflection of B-Kα line, the film thickness ratio of the reflecting layers 31 relative to the spacer layers 32 is preferred to be 1:1. It is to be noted that unlike the conventional case, selection of the film thickness ratio in the practice of the present invention is not always critical by the reason which will be described later.

Figure 2:
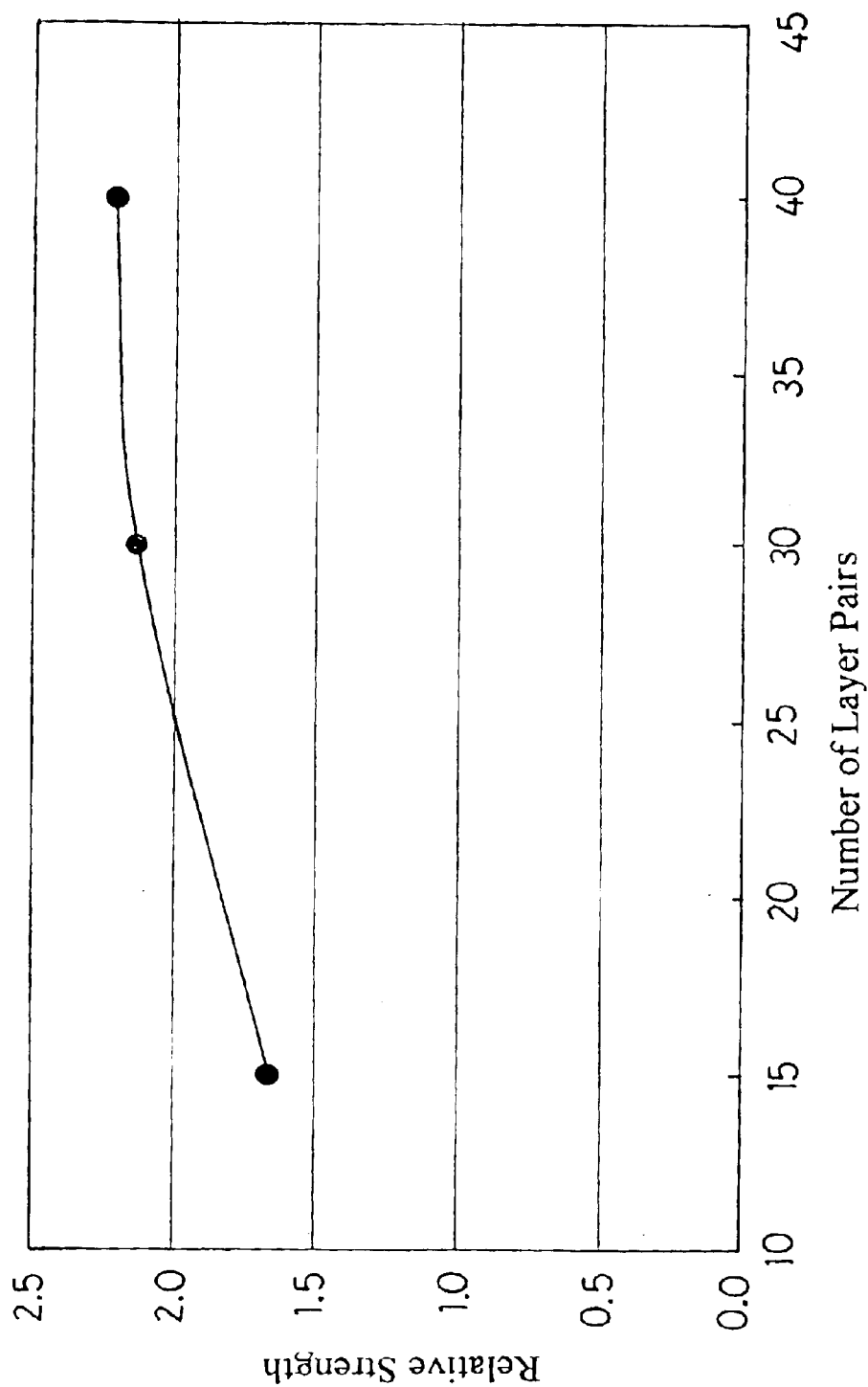
FIG. 2 is a characteristic chart showing the dependency of the strength of reflection of B-Kα line on the number of layer pairs in the spectroscopic device.

When based on Table 1 change in relative reflection strength that occurs when the periodic length is chosen to be 8 nm, the film thickness ratio is chosen to be 1:1 and the number of the layer pairs is chosen to be within the range of 15 to 40 is plotted in a chart, it will readily be seen from the chart of FIG. 2 that the relative reflection strength substantially saturates when the number of the layer pairs is chosen to be 35. In other words, when the number of the layer pairs is chosen to be 35, the strength of reflection of B-Kα line will be 98% of the saturation value exhibited when the number of the layer pairs is 40. Saturation of the reflection strength is affected only by the total laminated film thickness t (FIG. 1) that is equal to the product of the periodic length d multiplied by the number of the layer pairs, and since even if the periodic length d changes the total laminated film thickness that eventually results in saturation of the reflection strength remains the same, the present invention chooses the total laminated film thickness t (corresponding to a value equal to or higher than 280 nm) at which the strength of reflection of B-Kα line attains a value not lower than 98% (i.e., quite naturally lower than 100%) of the saturation value, so that the strength of reflection of B-Kα can be increased for the purpose of the present invention. More specifically, in the practice of the present invention, the number of the layer pairs when the periodic length is 8 nm suffices to be within the range of 35 to 40 and, hence, the total laminated film thickness t is preferably within the range of 280 to 320 nm.

Figure 3:
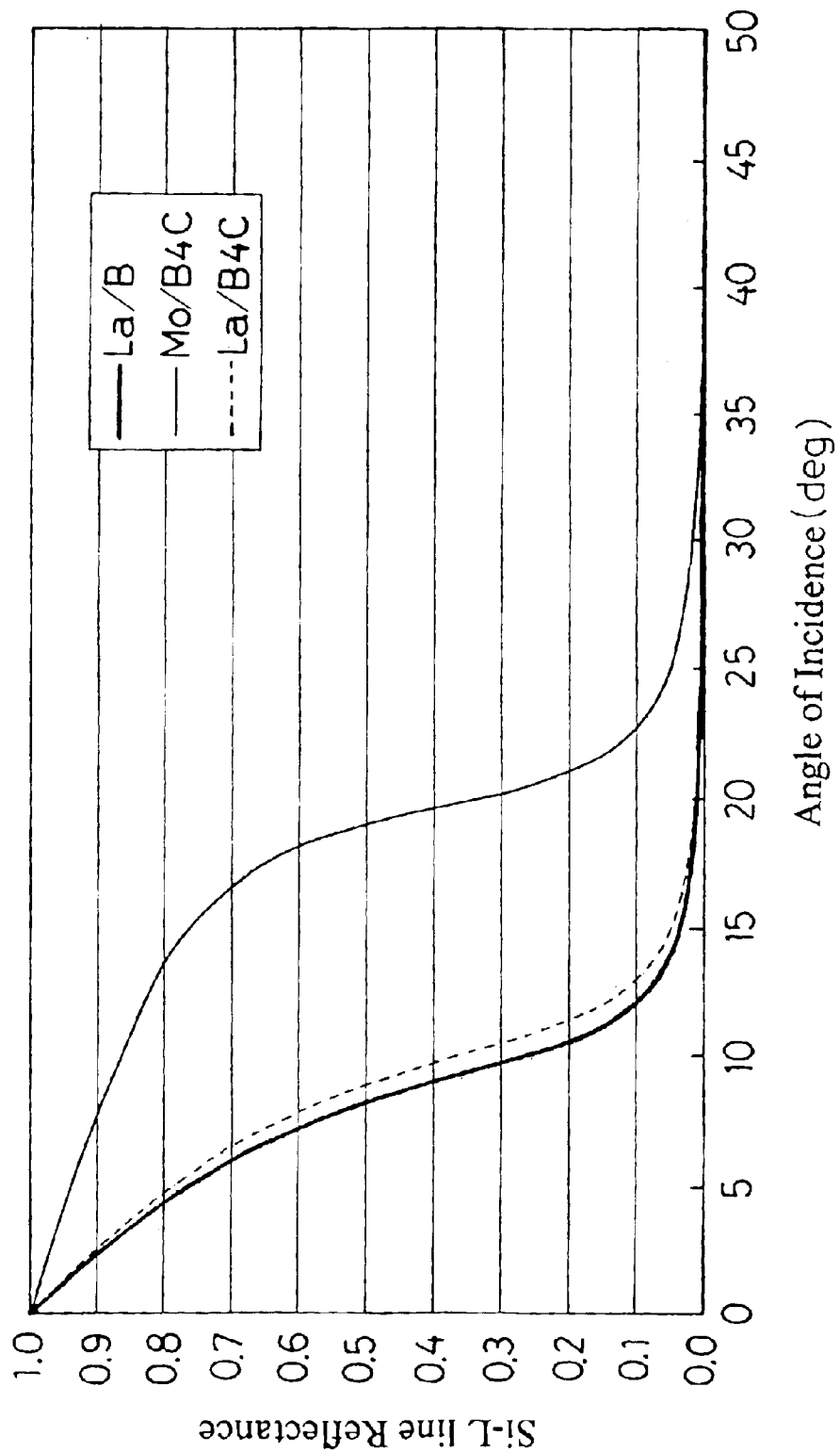
FIG. 3 is a characteristic chart showing the dependency of the total reflection strength of Si-L line on the angle of incidence exhibited by the conventional spectroscopic device and that of the present invention.

For example, when it comes to analysis of a trace quantity of boron contained in a thin film formed on a silicon wafer, a problem has been found in that Si-L line emitted from the wafer tend to undergo total reflection upon a surface of a spectroscopic device, resulting in noises background to B-Kα line. In view of this, with respect to the conventional Mo/B$_4$C based and La/B$_4$C based multilayered spectroscopic devices and the La/B based multilayered spectroscopic device of the present invention, theoretical simulated tests were conducted to determine the dependency of the total reflection strength of Si-L line on the angle of incidence, results of which are shown in the graph of FIG. 3. According to the graph of FIG. 3, it is clear that the La/B based multilayered spectroscopic device has shown, at all practical angles of incidence, the reflectance of Si-L line that is lower than that exhibited by any of the Mo/B$_4$C based and La/B$_4$C based multilayered spectroscopic devices.

Also, the periodic length of the Mo/B$_4$C based multilayered spectroscopic device is generally about 8 nm and in such case the angle of incidence of a peak of B-Kα line would be about 25°. If the reflectance of Si-L line at such angle is taken as a target value, the angle of incidence achieved with the La/B based multilayered spectroscopic device at which the reflectance of Si-L line attains a value about equal to the target reflectance would be about 14°. Considering that the periodic length of the multilayered spectroscopic device exhibiting a peak value of B-Kα line at that angle of incidence is about 14 nm, the periodic length d of the La/B based multilayered spectroscopic device according to the present invention will be 14 nm at maximum if the reflectance of Si-L line can be tolerated to a value about equal to that exhibited by the conventional Mo/B$_4$C based multilayered spectroscopic device. It is, however, to be noted that even if the reflectance of Si-L line which provides the background attains a value about equal to that exhibited with the conventional Mo/B$_4$C based multilayered spectroscopic device, increase of the strength of reflection of B-Kα line to be analyzed as discussed above effectively improves over the P/B ratio (peak/background ratio) as compared with that of the conventional multilayered spectroscopic device and the influence which would be brought about by Si-L line can therefore be reduced.

On the other hand, if the total laminated film thickness t remains the same, the smaller the periodic length is, the more considerable the reduction of the reflection strength attributable to the roughness at the interlayer surface. However, a series of experiments conducted to determine the lowermost limit of the periodic length d at which as compared with the conventional Mo/B$_4$C multilayered spectroscopic device the strength of reflection of B-Kα that has increased about 2.2 times that exhibited by the conventional multilayered spectroscopic device as shown in FIG. 2, it has been that the lowermost limit of the periodic length d is 7 nm. Accordingly, in terms of both the reduction of the influence brought about by Si-L line that provide the background and the increase of the strength of reflection of B-Kα line, the periodic length d that is to be employed in the practice of the present invention is preferred to be within the range of 7 to 14 nm.

There is another problem: In an analysis of boron contained in a sample together with oxygen, third order line of O-K line that are the fluorescent X-rays emitted from oxygen are reflected by the spectroscopic device to such an extent as to result in interfering X-rays in the vicinity of B-Kα line to be analyzed. In the conventional Mo/B$_4$ based multilayered spectroscopic device, the film thickness ratio of the reflecting layers relative to the spacer layer has been strictly chosen to be 1:2 in order to reduce the third order reflection of O-K line. In contrast thereto, in the La/B based multilayered spectroscopic device of the present invention, although the film thickness ratio of the reflecting layers 31 relative to the spacer layers 32 is appropriately chosen to 1:1 in order to increase the strength of reflection of B-Kα line by the reasons as hereinbefore discussed, a question would arise that if the film thickness ratio is chosen to be 1:1 in the multilayered spectroscopic device of the present invention, the third order reflection of O-K line will bring about undesirable influences more considerable than that with the conventional multilayered spectroscopic device.

Figure 4:
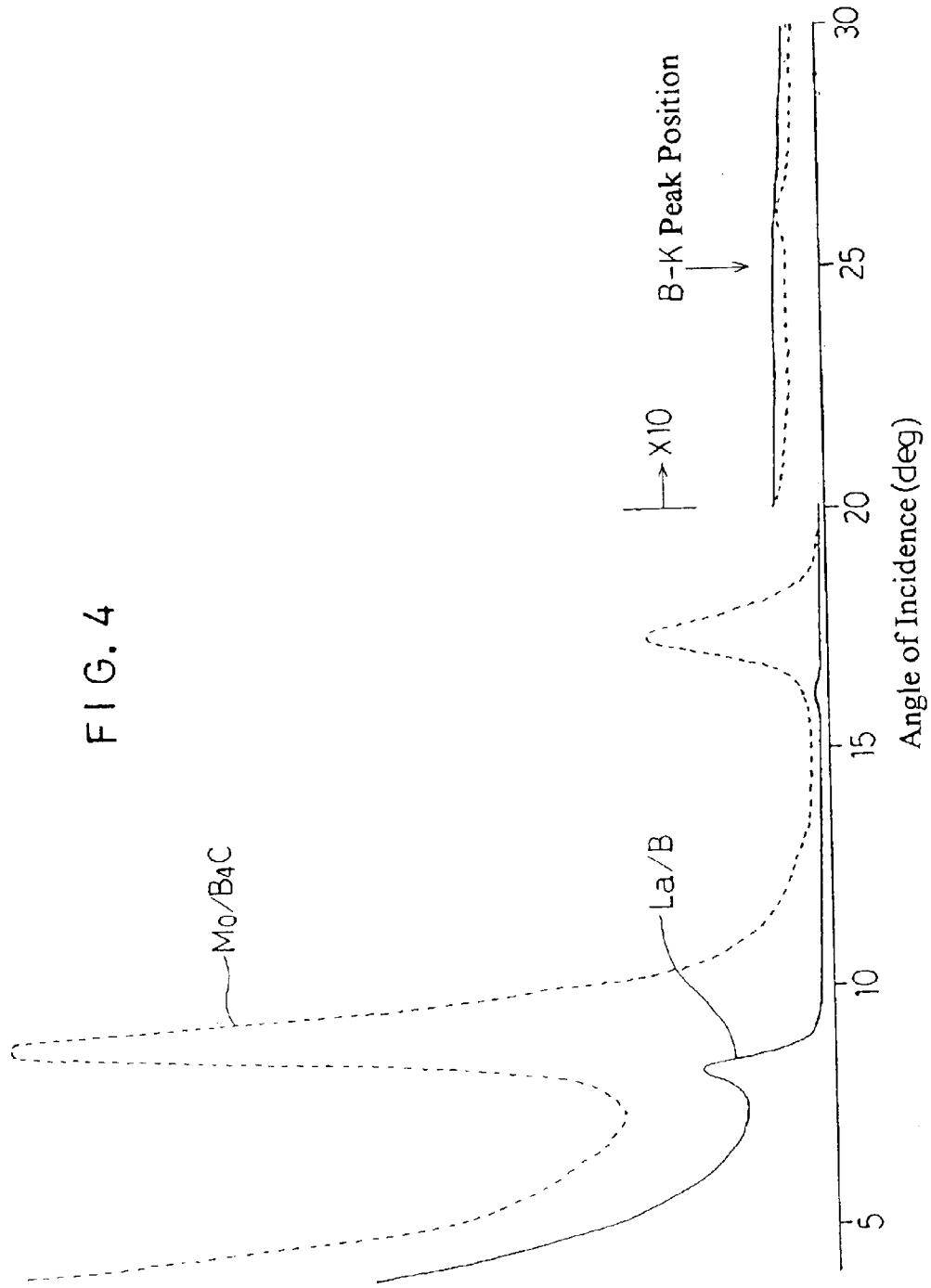
FIG. 4 is a characteristic chart showing the influence brought about by third-order reflection of O-K line at an angle of emergence of B-Kα line exhibited by the conventional spectroscopic device and that of the present invention.

In view of the foregoing, with respect to the conventional Mo/B$_4$C based multilayered spectroscopic device and the La/B based multilayered spectroscopic device of the present invention, and using a sample in the form of a quartz glass (SiO$_2$) that is a typical oxygen containing material, a series of experiment have been conducted to determine the influences brought about by the third order reflection of O-K line at the angle of emergence of B-Kα line, results of which are shown in the graph of FIG. 4. According to the graph of FIG. 4, it is clear that with the La/B based multilayered spectroscopic device of the present invention the capability of reflecting O-K line is basically extremely low and, accordingly, the influences which would be brought about by the third order reflection are so minimal as to be negligible.

In other words, unlike the conventional Mo/B$_4$C based multilayered spectroscopic device, the La/B based multilayered spectroscopic device of the present invention is such that the film thickness ratio of the reflecting layers 31 relative to the spacer layers 32 need not be specifically set in order to reduce the third order reflection of O-K line. As hereinbefore discussed, to increase the strength of reflection of B-Kα line it is sufficient for the film thickness ratio of the reflecting layers 31 relative to the spacer layers 32 to be set to 1:1 and, in such case, the film thickness ratio need not be so strict as to be the case in which the third order reflection of O-K line is reduced. That is to say, in the practice of the present invention, the film thickness ratio of the reflecting layers 31 relative to the spacer layers 32 may not be strictly 1, but may be sufficiently within the range of 2/3 to 3/2 and preferably within the range of 4/5 to 5/4.

Summarizing the foregoing discussion as to the numerical limitations, in the practice of the present invention the periodic length d is chosen to be within the range of 7 to 14 nm and the film thickness ratio of the reflecting layers 31 relative to the spacer layers 32 is chosen to be within the range of 2/3 to 3/2 and preferably 4/5 and 5/4. If in a condition in which the periodic length d and the film thickness ratio are determined, the total laminated film thickness t is increased, the strength of reflection of B-Kα line will increase and be eventually saturated, and accordingly the total laminated film thickness t is chosen to be a value equal to or higher than 98% of the saturation value of the reflection strength and, preferably, within the range of 280 to 320 nm. According to Table 1 and FIG. 2, for example, in the embodiment in which the periodic length is chosen to be 8 nm, the film thickness ratio is chosen to be 1 and the total laminated film thickness is chosen to be within the range of 280 to 320 nm (corresponding to the use of 35 to 40 layer pairs), the strength of reflection of B-Kα is about 2.2 times that exhibited by the conventional Mo/B$_4$C based multilayered spectroscopic device and, on the other hand, in the embodiment in which the periodic length is chosen to be 13 nm, the film thickness ratio is chosen to be 1 and the total laminated film thickness is chosen to be 312 nm (corresponding to the use of 24 layer pairs), the strength of reflection of B-Kα is about 3.8 times that exhibited by the conventional Mo/B$_4$C based multilayered spectroscopic device. In those embodiments, as discussed above, the influences brought about respectively by the third order reflection of O-K line that provide the interfering X-rays and Si-L line that provide the background can be sufficiently reduced simultaneously.

In the next place, by changing the material for the reflecting layers 31 to a lanthanum alloy containing lanthanum and molybdenum in an atomicity ratio of 9:1, a spectroscopic device in which the periodic length is 8 nm, the film thickness ratio is 1:1 and the total laminated film thickness is 320 nm (corresponding to the use of 40 layer pairs) was prepared in the same manner as hereinbefore described. With this (La, Mo)/B based multilayered spectroscopic device, it has been found that as compared with the previously discussed La/B based multilayered spectroscopic device having the same periodic length and other numerical values, the strength of reflection of B-Kα has been found increasing by about 10%. It appears because while a thin film of a pure metal generally tends to easily form a polycrystalline film and also to form a compound, this tendency is suppressed by the use of the alloy and, hence, a flat interface of a small roughness could have been obtained. It is to be noted that the influences brought about respectively by the third order reflection of O-K line that provide the interfering X-rays and Si-L line that provide the background can be reduced by a quantity similar to that with the La/B based multilayered spectroscopic device.

Also, by changing the material for the reflecting layers 31 to a lanthanum oxide (La$_2$O$_3$), a spectroscopic device in which the periodic length is 8 nm, the film thickness ratio is 1:1 and the total laminated film thickness is 320 nm (corresponding to the use of 40 layer pairs) was prepared in the same manner as hereinbefore described. With this La$_2$O$_3$/B based multilayered spectroscopic device, it has been found that as compared with the previously discussed La/B based multilayered spectroscopic device having the same periodic length and other numerical values, the strength of reflection of B-Kα has been found substantially identical. The influences brought about respectively by the third order reflection of O-K line that provide the interfering X-rays and Si-L line that provide the background can be reduced by a quantity similar to that with the La/B based multilayered spectroscopic device. The La$_2$O$_3$/B based and La/B based multilayered spectroscopic devices in those respective embodiments and the conventional La/B$_4$C based multilayered spectroscopic device were tested as to their durability under a high humidity atmosphere of a 100% relative humidity. As a result of the tests, while an apparent change in quality has been found in the La/B based and La/B$_4$C based multilayered spectroscopic devices in such a way that one day after the durability test a surface of each of those multilayered spectroscopic devices has been whitened along with a localized exfoliation, no change in quality has been found in the La$_2$O$_3$/B based multilayered spectroscopic device even after about one month subsequent to the durability test and has, thus, exhibited a high resistance to humidity. This appears to have resulted from the fact that while lanthanum has a very high reactivity, the use of the lanthanum oxide has rendered the multilayered spectroscopic device to be very stable even when exposed to an oxidization in the high humidity atmosphere.

As discussed in the foregoing, with the multilayered spectroscopic device for use in fluorescent X-ray analysis of boron according to the present invention, as compared with the conventional Mo/B$_4$C based multilayered spectroscopic device, not only can the influences brought about respectively by the third order reflection of O-K line that provide the interfering X-rays and Si-L line that provide the background be reduced sufficiently, but also the strength of reflection of B-Kα line can be increased to a value that is about 2.2 to 3.8 times that exhibited by the conventional multilayered spectroscopic device and, even compared with the conventional La/B$_4$C based multilayered spectroscopic device, the strength of reflection of B-Kα can be increased to a value that is by a factor of about 1.3 and, therefore, the fluorescent X-ray analysis of boron can be achieved highly accurately in a short length of time.

What is claimed is:

1. A multilayered spectroscopic device for use in fluorescent X-ray analysis of boron (B) contained in a sample, which device comprises a plurality of layer pairs, each pair including a reflecting layer and a spacer layer, that are laminated on a substrate;

wherein lanthanum (La), an alloy containing lanthanum as a principal component or lanthanum oxide (La$_2$O$_3$) is used as material for the reflecting layers, and boron is used as material for the spacer layers, a periodic length is chosen to be within the range of 7 to 14 nm and a film thickness ratio of the reflecting layers relative to the spacer layers is chosen to be within the range of 2/3 to 3/2; and wherein the multilayered spectroscopic device has a total laminated film thickness sufficient to allow a strength of reflection of B-Kα line to attain a value equal to or higher than 98% of a saturation value.

2. The multilayered spectroscopic device for use in fluorescent X-ray analysis of boron as claimed in claim 1, wherein the total laminated film thickness is chosen to be within the range of 280 to 320 nm.

3. The multilayered spectroscopic device for use in fluorescent X-ray analysis of boron as claimed in claim 1, wherein the film thickness ratio of the reflecting layers relative to the spacer layer is chosen to be within the range of 4/5 to 5/4.

* * * * *